(12) United States Patent
Bublewitz et al.

(10) Patent No.: US 8,308,480 B2
(45) Date of Patent: Nov. 13, 2012

(54) METHOD AND KIT FOR PRODUCING A DENTAL PRODUCT

(75) Inventors: Alexander Bublewitz, Herborn (DE); Jens-Peter Reber, Meinerzhagen (DE); Matthias Suchan, Hachenburg (DE)

(73) Assignee: Kettenbach GmbH & Co. KG, Eschenburg (DE)

( * ) Notice: Subject to any disclaimer, the term of this patent is extended or adjusted under 35 U.S.C. 154(b) by 149 days.

(21) Appl. No.: 12/473,099

(22) Filed: May 27, 2009

(65) Prior Publication Data

US 2009/0298018 A1  Dec. 3, 2009

(30) Foreign Application Priority Data

May 27, 2008  (DE) .......................... 10 2008 025 275
Feb. 19, 2009  (DE) ...................... 20 2009 002 364 U

(51) Int. Cl.
*A61C 9/00* (2006.01)

(52) U.S. Cl. ........................................ 433/48; 433/37

(58) Field of Classification Search .................. 433/37, 433/40, 48, 213, 214, 215
See application file for complete search history.

(56) References Cited

U.S. PATENT DOCUMENTS

| | | | | |
|---|---|---|---|---|
| 3,473,225 A | * | 10/1969 | Walker et al. .................... 433/48 |
| 4,146,963 A | * | 4/1979 | Schreinemakers .............. 433/37 |
| 4,867,680 A | * | 9/1989 | Hare et al. ........................ 433/37 |
| 5,031,638 A | * | 7/1991 | Castaldi .......................... 128/861 |
| 5,076,791 A | | 12/1991 | Madray, Jr. |
| 5,415,544 A | * | 5/1995 | Oxman et al. ................... 433/48 |
| 5,769,633 A | * | 6/1998 | Jacobs et al. .................... 433/37 |
| 6,247,926 B1 | * | 6/2001 | Thornton ......................... 433/48 |
| 6,364,665 B1 | * | 4/2002 | Trettenero ..................... 433/215 |
| 2002/0144694 A1 | * | 10/2002 | Kittelsen et al. .............. 128/861 |
| 2006/0093983 A1 | | 5/2006 | Schultz |
| 2006/0269904 A1 | * | 11/2006 | Suchan et al. ................ 433/213 |

FOREIGN PATENT DOCUMENTS

| | | |
|---|---|---|
| DE | 10349047 B3 | 2/2005 |
| DE | 102006056983 A1 | 6/2008 |
| WO | 2005/113675 A2 | 12/2005 |
| WO | 2008/064904 A1 | 6/2008 |

* cited by examiner

*Primary Examiner* — Ralph Lewis

(74) *Attorney, Agent, or Firm* — McDonnall Boehnen Hulbert & Berghoff LLP

(57) ABSTRACT

The invention relates to a method and a kit for producing a dental product. The invention also relates to a device that allows the method according to the invention to be implemented. According to the invention, a thermoplastic material (4) of said kit is selectively heated through the supply of targeted (directed) energy more strongly than an impression tray (1) and/or an impression material (3).

11 Claims, 2 Drawing Sheets

METHOD AND KIT FOR PRODUCING A DENTAL PRODUCT

CROSS-REFERENCE TO RELATED APPLICATIONS

This application claims priority under 35 U.S.C. §119(a)-(d) to German patent applications no. 10 2008 025 275.1, filed May 27, 2008, and no. 20 2009 002 364.8, filed Feb. 19, 2009, each of which is hereby incorporated by reference in its entirety.

BACKGROUND OF THE INVENTION

1. Field of the invention

The invention relates to a method and a kit for producing a dental product. The invention also relates to a device that allows the method according to the invention to be implemented.

2. Technical Background

A dental product in the sense of the present invention is taken to mean, for example, an orthodontic aligner, a bite plate, a miniature plastic splint, an occlusal splint, a healing cap, a fluidisation tray, a whitening tray, a transfer tray, a mouth protector, a positioner or a medication carrier made of a thermoplastic material. However, a dental product can also be a dental impression, e.g. a negative mold of the dental situation which can, for example, be preserved in the form of a hardened thermoplastic film. In a similar way to traditional dental impression materials, from such a casting a working model for the further production of dentures can be produced by filling with a modelling material such as plaster.

A dental product in the form of a splint for orthodontic treatment is known, for example, from US 2006/0093983 A1. In DE 103 49 047 B3 a method of producing a dental splint is described in which an impression tray is coated with a plastically moldable materials on which a thermoplastic film is provided, which can be heated, for example in a water bath, together with the plastically moldable material, or separately from it. In this warmed state the thermoplastic film is plastically moldable and can be applied directly into the mouth of a patient to produce the dental splint. To this end the thermoplastic material is applied to the teeth and/or the gums. After cooling of the thermoplastic film to body temperature it hardens and in this condition it can easily be removed from the patient's mouth.

In WO 2005/113675 A2 a method of individually adapting a prefabricated dental splint is described. For this the dental splint should be heated in a water bath or wrapped in a dampened cloth and heated in a microwave oven before being adjusted in the mouth. In addition, methods are known from U.S. Pat. No. 5,076,791 and U.S. Pat. No. 6,364,665 in which a thin thermoplastic material is heated in boiling water, for example, in order to then be adapted to the teeth in the mouth. These methods conceal the danger that increased heat input through the strongly heated splint can be experienced as unpleasant, or even result in injury.

Under the name "Erkoform 3d" the company ERKODENT Erich Kopp GmbH, 72285 Pfalzgrafenweiler, Germany, also supplies a deep drawing device with which dental splints can be produced from a plate or film of thermoplastic material on a plaster model. This device is equipped with a heat radiator under which the thermoplastic materials can be heated and plastified while clamped in a frame. In this state the thermoplastic material can be applied to the plaster model in order to produce a splint adapted to the outer contours of the plaster model using deep drawing technology in a vacuum. Although this device is suitable for use in a dental laboratory, it is not suitable for producing a splint or similar dental product intraorally, i.e. in the patient's mouth.

In DE 10 2006 056 983 A1 the use of a thermoplastic material is proposed for producing a dental product which is selected from the following group: copolymers of ethylene and vinyl acetate, polycaprolactone, polypropylene, polyethylene, polybutenene, styrene-isoprene-styrene and/or styrene-butadiene-styrene copolymers, thermoplastic elastomers, amorphic polyolefins, linear thermoplastic polyurethanes, copolyesters, polyamide resins, polyamide/EVA-copolymers, polyaminoamides based on dimer fatty acids, polyesteramides, polyetheramides or a shape memory synthetic material.

In terms of their thermal and Theological properties, E/VA (ethylene/vinyl acetate copolymer) and PCL (poly(epsilon-caprolactone)) are very suitable for use in a thermoplastic splint system, i.e. to produce a dental product. However, because of its low level of hardness and its low E-module, pure ENA is only suitable to a very limited extent for such dental indications, which require hard materials. Although on the other hand pure PCL exhibits very good mechanical properties, it is not, however, transparent, which for aesthetic reasons and possibly during treatment using light, can be considered as disadvantageous. The optically highly transparent and medium-hard E/AA (ethylene/acryl acetate copolymer) is not suitable for forming a dental splint in the patient's mouths due to its very high elastic portion in the soft state at 85° C.

SUMMARY OF THE INVENTION

One aspect of the invention is a method comprising the following steps: initially an impression tray filled with impression material is provided, whereby a thermoplastic material for producing a dental product is envisaged on or in the impression tray and/or the impression material. The thermoplastic material applied on or in the impression tray and/or the impression material is then heated to a temperature below 200° C. and above the softening temperature of the thermoplastic material. This temperature is particularly preferably located in a range between around 40° C. and 80° C. The thermoplastic material with the impression tray filled with impression material is then applied into the mouth of the patient where the thermoplastic material forming a dental product is applied to at least one tooth and/or the gum for a period of time until the thermoplastic material has cooled to a temperature below its softening temperature. The impression tray, the impression material and the dental product formed from the thermoplastic materials are then removed from the patient's mouth. The thermoplastic material is heated more strongly than the impression tray and/or the impression material. This takes place in particular through the supply of targeted, i.e. directed, energy.

Targeted energy for the selective heating of essentially only the thermoplastic materials is taken to mean the specific supply of energy, mainly coming from one direction for example. In contrast to warming in a water bath or in an oven, such as a microwave oven, the heat energy can be specifically directed onto the thermoplastic material so that it is almost exclusively, or at least more strongly, heated than the impression tray and the impression material. With regard to the present invention, initially stronger heating of the thermoplastic material to attain its softening temperatures compared with heating the impression tray and/or the impression material is the relevant factor, irrespective of whether during sufficiently long heat supply the temperatures of the thermoplastic material, the impression tray and the impression material come to approximate each other. In other words, in accordance with the invention the thermoplastic material is initially heated more strongly than the impression tray and/or the impression material until the deformability required for producing the dental product is achieved. The thermoplastic material is then applied as quickly as possible, i.e. without the thermoplastic material cooling too strongly and/or the impression tray and/or impression material heating up too strongly. The selective stronger heating of the thermoplastic material can also be understood as targeted heat supply that can be interrupted or stopped at a point in time before the impression tray and/or the impression material heat up to too much.

In accordance with certain embodiments of the invention, a heat radiator, a lamp and/or a source of hot air are particularly suitable as a source of energy for the selective heating of the thermoplastic material.

In addition to the targeted heating of the thermoplastic material, it can be provided with a substance that improves the heat input into the thermoplastic material and/or reduces the heat input into the impression tray and/or the impression material. In the same way the impression tray and/or the impression material can be provided with a substance, or consist of a substance, that reduces heat input into the impression tray and/or into the impression material. Such substance can be matched to a particular source of energy as an activator or receptor in order to support the selective heating of a material or to prevent the heating of another material. Such substances are described, for example, in the international patent application PCT/EP2007/010414, which is hereby incorporated by reference in its entirety.

The stronger heating of the thermoplastic material compared with the impression material and/or the impression tray can be further supported in that at least one insulation layer and/or insulation solution is provided between the thermoplastic material and the impression material. This insulation layer or insulation solution can bring about a thermal decoupling between the thermoplastic material and the impression material and/or facilitate loosening of the thermoplastic material from the impression material. In addition, or alternatively to the insulation layer and/or the insulation solution, an air cushion can be provided between the thermoplastic material and the impression material which makes heat transfer from the thermoplastic material to the impression material more difficult or retards it.

In accordance with a particularly preferred embodiment of the invention heating of the thermoplastic material only takes place up to a defined temperature which can be indicated by use of a temperature indicator in and/or on the impression tray, the impression material, the thermoplastic material and/or the insulation layer, more particularly by way of a change of color. In this way it is easy for a user to recognise sufficient heating of the thermoplastic material and to discontinue further heat supply, which either heats the thermoplastic material too much or supplies too much thermal energy into the impression material and/or the impression tray.

The use of the method in accordance with the invention can also be facilitated by prefabricating the thermoplastic material and the impression material and only having to introduce them into the impression tray before the first step of the procedure. For this, the thermoplastic material can, for example, be in the form of a sausage-skin-like tube in which the impression material is taken up. After cooling of the thermoplastic material the dental product can be cut out of the sausage-skin-like tube.

The method in accordance with the invention can be particularly easily implemented if the impression tray, the impression material and the thermoplastic material/the dental product formed therefrom, can be jointly removed as an entity from the patient's mouth. However, in some cases of application it may be advantageous to initially only remove the impression tray and/or the impression material, while at least the thermoplastic material remains in the patient's mouth for further adaptation.

Another aspect of the invention is a kit for producing a dental product, which, in particular, is also suitable for use in the above-described procedure. A kit or set is a specially ready-prepared combination of several elements. The kit in accordance with the invention consists of an impression tray made of a material that is solid at temperatures below around 110° C., more particularly below around 150° C., and which has a base that is matched to the shape of a jaw with side walls projecting away from this, an impression material provided in or on the impression tray that is plastically deformable, at least at temperatures between 10° C. and 90° C., and a thermoplastic film for producing, for example, a splint-like dental product, which is solid at body temperature and can be plastically molded by hand at a temperature between body temperature and around 150° C. Here, the thermoplastic film is formed with a first section matched to the shape of the jaw which is arranged on the side of the impression material facing away from the base of the impression tray, and from which edge sections project, which at least in parts overlap and/or cover internally and externally the side walls of the impression tray. In accordance with one example of embodiment, between the first section of the thermoplastic film and the impression material an air cushion can be provided, at least in parts, which, for example can be a continuous air cushion or consist of several smaller air cushions or air bubbles. The air cushion ensures that the heat transfer between the thermoplastic film and the impression material is made more difficult and/or is retarded. This means that particularly in the case of the supply of targeted heat energy to the thermoplastic film, the film heats up more strongly and/or more rapidly than that impression tray and/or the impression material.

If, as described above, the thermoplastic film is pulled with its edge sections over the side walls of the impression tray, this prevents the impression material from unintentionally coming out of the impression tray. In addition, the neck of the tooth and/or the gum can also be clearly recorded which is of relevance, particularly when using the dental product produced from the thermoplastic film as a dental splint. If the thermoplastic film closely fits onto the impression tray, i.e. essentially without any play, the thermoplastic film does not become deformed during heating, or if so at least only slightly.

It has been proven to be particularly advantageous if the material of the thermoplastic film is selected from the following group: ethylene-acrylic acid copolymer (for example Nucrel® 2806 (DuPont™)), copolymers of ethylene- and vinyl acetate, copolymers of ethylene and methylethacrylate, polycaprolactone, polypropylene, polyethylene, polybutenene, styrene-isoprene-styrene and/or styrene-butadiene-styrene-copolymers, thermoplastic elastomers, amorphic polyolefines, linear thermoplastic polyurethanes, copolyesters, polyamide resins, polyamide/EVA-copolymers, polyaminoamides based on dimer fatty acids, polyesteramides, polyetheramides, polyvinylchlorides, cellulose ester, such as cellulose acetate, cellulose proprionate, cellulose butyrate, polylactic acid, polyhydroxibutyrates or a shape-memory synthetic material and mixtures of the above synthetic materials. With sufficient heating these materials can be plastically deformed and after cooling they retain a certain elasticity, which facilitates their removal from the month without destroying the shape of the dental product.

In order to produce a dental product, the thermoplastic film should be of sufficient thickness in order to prevent the tearing or biting through of the film. On the other hand the thermoplastic film should also not be too thick so that rapid heating and cooling are possible. It is preferable if the thermoplastic film has a layer thickness of between around 0.1 mm and around 4 mm, more particularly between around 0.5 mm and around 2.5 mm.

Depending on the dental product that is to be produced using the method in accordance with the invention, it may be advantageous if the thermoplastic material and the impression material can be separated from each other more easily or with more difficulty. Thus, in order to produce a dental impression as a dental product it is preferable if the impression material is formulated to be so sticky that the adhesive bond between the impression material and the thermoplastic material is greater than the pull-off forces occurring during removal of the dental product from the mouth of the patient. As a development of this inventive idea it is preferable if the impression material is also formulated to be so sticky that the adhesive bond between the impression material and the impression tray is greater than the pull-off forces occurring during removal of the dental product from the mouth of the patient. The adhesive bond between the impression material and the impression tray and/or the thermoplastic material can also be achieved with mechanical and/or with chemical bonding means.

In contrast, for the production of a dental splint as a dental product it is preferable if only the impression tray and the impression material are, for example, adhesively bonded to each other, while the thermoplastic material can easily be loosened from the impression material and the impression tray. For producing a dental splint it is also preferable if the substances of the thermoplastic film and/or the impression material are selected and/or equipped in such a way that at least between the thermoplastic film and the impression material no adhesion forces are formed. The detaching of a dental splint made of thermoplastic film from the impression material can also be further facilitated by providing between the thermoplastic film and the impression material at least one insulating layer in the form of an insulating film, insulating foil and/or insulating solution.

In order to avoid unintentional loosening of the impression material from the impression tray, particularly during removal, in accordance with a preferred form of embodiment of the invention it is envisaged that the impression tray and the impression material are connected to each other by way of a mechanical retention device and/or an adhesive bond. This may be achieved by providing holes in the impression tray.

The impression material essentially serves to adapt the thermoplastic film well to the dental situation and/or the edge of the gums, including in areas of undercutting. Impression material is taken to mean any suitable material that is sufficiently elastically or plastically deformable to apply and to adapt the thermoplastic material to teeth. For this the impression material preferably exhibits a viscosity of over around 1000 Pa·s, preferably up to 150.000 Pa·s. These viscosities are in accordance with consistencies measured according to the consistency measurement of ISO 4823 of 15 to 30 mm, more particularly between 20 and 25 mm.

If the impression tray, the impression material, the thermoplastic film and/or the insulating material and/or the insulating layer have a temperature indicator, the user can quickly recognise when the thermoplastic film has reached a temperature that is sufficient for being worked. It can also be shown when the temperature of the impression tray, the impression material or the thermoplastic film is so high that optimum processing is not possible or there is even a risk of injuring the patient. These temperature indicators can, for example, comprise a thermal strip or a thermal color or similar temperature sensor.

Irrespective of the features mentioned previously, a dental product in accordance with one embodiment of the invention that has, for example, been produced by use of a kit of the type described above, consists of a thermoplastic material that has been selected from the following group: compounds and blends of ethylene/vinyl acetate-copolymer (E/VA) and poly(epsilon-caprolactone) (PCL), compounds and blends of ethylene/vinyl acetate copolymer (ENA) and ethylene/acryl acetate copolymer (E/AA), compounds and blends of ethylene/acryl acetate copolymer (E/AA) and poly(epsilon-caprolactone) (PCL), as well as trans-1,4-polyisoprene.

In certain aspects, the invention is based on the idea that various requirements are set for the synthetic materials with a low melting point for use in a dental product, for example, a splint, which can be particularly well met by the materials mentioned above. In addition to a softening point of 65 to 85° C., which is tolerable to patients, depending on the indication and area of application of the dental product, various mechanical properties are desired (e.g., Shore hardness, heating module, bending strength). With regard to this it is particularly difficult to find synthetic materials that at the same time as having a low melting point, also exhibit a high degree of hardness, heating module and bending strength. Furthermore, on the grounds of good aesthetics of the subsequent splint, the synthetic materials should be transparent if possible.

The central measuring method for characterising the low-melting point synthetic materials are temperature-dependent oscillation-rheometer tests with which the elastic and viscous behaviour of the synthetic materials can be shown in heating and cooling curves, and with which conclusions can be drawn about the actual behaviour of the various synthetic materials during the real processing stages "softening in the heating module", "shaping in the mouth" and "wearing the splint in the mouth".

In accordance with a preferred embodiment, the thermoplastic material of the dental product is a blend or compound consisting of around 99 to around 30% by weight, more particularly around 95 to around 70% by weight ethylene/vinyl acetate copolymer (ENA) and around 1 to around 70% by weight poly(epsilon-caprolactone) (PCL), whereby a proportion of around 5% by weight PCL at around 95% E/VA as well as around 25% by weight PCL at around 75% by weight ENA is particularly preferred. With still acceptable transparency, such blends of E/VA and PCL exhibit an improvement in mechanical properties compared with pure E/VA and a decrease in the gel temperatures in the rheological heating and cooling curves, which has a positive effect on the shaping and wearing properties of the splint. In addition, E/VA, PCL and their blends exhibit very positive properties in terms of temperature-dependent rheological behaviour. In the heating curve, which simulates the softening procedure in a heating module ("targeted heat"), at 85° C., which is the maximum temperature tolerated by patients, all the materials are sufficiently plastic for shaping and only have slight disruptive elastic portions.

As an alternative to this the thermoplastic material can be a blend or compound of around 99 to around 30% by weight, more particularly round 95 to around 70% by weight ethylene/vinyl acetate copolymer (ENA) and around 1 to around 70% by weight, more particularly around 5 to around 30% by weight ethylene/acryl acetate copolymer (E/AA).

In the cooling curve, in the case of these particularly suitable materials so-called plateaus can be determined. In spite of continuing cooling the material does not harden as quickly as would be expected from the heating curve (hysteresis). The plasticity is retained down to lower temperatures (e.g. to around 60° C.).

Fundamentally it is preferred if the heating and cooling behaviour of the thermoplastic material exhibits a hysteresis effect which on cooling exhibits a plastic deformability at lower temperatures than during heating. This assists the shaping procedure during the production of the splint as the materials can already cool on the way from the heating module or suchlike into the patient's mouth, but will then still be suitable for the shaping procedure, i.e. they are still sufficiently plastic and the lower temperature is more acceptable to the patient. At mouth temperature, i.e. with a safety margin at 45° C., the materials are sufficiently hardened again that they can withstand the mechanical stressing in the mouth without permanent deformation.

For good manipulation it is preferable if at a temperature of around 60° C. to around 90° C., more particularly at around 85° C. the thermoplastic material is sufficiently plastic to be shaped and only exhibits very small elastic portions.

The kit in accordance with the invention is preferably characterised in that the impression tray and the thermoplastic film (foil) are designed and arranged in such a way that the film is not in contact with the edge of the outer (vestibular) wall of the tray, at least not in the frontal dental area. In other words there is a space, preferably filled with impression material, between the circumferential edge facing away from the base of the impression tray and the inner side of the film (pre-form). This can be achieved by way of a greater height, at least in sections, of a side wall area of the film compared with the outer side wall. This embodiment is particularly preferred if the film is arranged with its side wall areas on the inside of the impression tray walls, that is between the impression material and the impression tray wall. Hereby, one edge of the side wall area of the film can be on the base of the impression tray. Alternatively a side wall area of the film can also be supported on the impression tray, overlapping the tray wall from outside or on radially outward projecting projections and/or the grip of the impression tray. By way of this arrangement of the film (pre-form) and the impression tray a constant flow of the film is facilitated during shaping.

The invention also relates to a device for the selective heating of a thermoplastic material, which can, more particularly, be used in a method of the type described above. The device according to the invention comprises an energy source, more particularly in the form of a heat radiator, such as infrared radiators in the form of contour, surface or omega radiators, or a lamp, for example, a fluorescent tube, halogen lamp, metal vapor lamp, gas discharge lamp, light diode or incandescent bulb and/or a source of warm air, and a holder device for a kit, which, for example, can be a kit of the type described above, comprising at least one impression tray, an impression material and the thermoplastic material to be heated. In accordance with the invention the holder device is arranged with regard to the energy source so that essentially only the thermoplastic material is exposed to the direct heat radiation of the energy source. The kit and the energy source are arranged in such a way that the thermoplastic material faces the source of energy.

In accordance with a preferred form of embodiment of the device according to the invention, means for the targeted guidance of the heat radiation of the energy source onto the thermoplastic material are provided between the energy source and the holder device. When using a source of warm air as the energy source, these means can, for example, be designed as a pipeline that directs the warm air onto the thermoplastic material. When using radiation, devices like mirrors, lenses and lightguides can direct the radiation onto the thermoplastic material.

The device in accordance with the invention can also be assigned a control or regulating device which on heating of the kit is switched on or off at a certain temperature, depending on either, for example, a predeterminable time setting and/or depending on a measuring parameter that records a defined state of the thermoplastic material. Such measuring parameters can be, for example, the temperature of the thermoplastic material, its consistency and/or its color.

The present invention provides a number of advantages. For example, in certain aspects, the methods and kits of the present invention allow a dental product can be produced intra-orally with a high degree of fitting precision without being found unpleasant by patients in terms of heat input.

DESCRIPTION OF THE DRAWINGS

The invention will be described in more detail below with the aid of examples of embodiment and with reference to the drawing.

Schematically.

DETAILED DESCRIPTION

FIGS. 1 to 3, 4 and 5 show an impression tray 1, which corresponds, for example, to a conventional impression tray for producing a denture mold with a thickness, for example, of 0.5 mm, 0.8 mm, 1.0 mm or 1.5 mm, from which a plaster model can be made. The impression tray 1 can be made of metal, or preferably a plastic, which at least at temperatures below 80° C., preferably also at temperatures below 120° C. is rigid and cannot essentially be deformed by hand. If the impression tray 1 is also form-stable at temperatures under 140° C., it can be sterilised in an autoclave. The impression tray 1 has a base that in a horseshoe-shape follows the contours of a set of teeth and, in the figures, has side walls extending upwards from the base so that the impression tray 1 is approximately U-shaped in cross-section.

Figure 1:
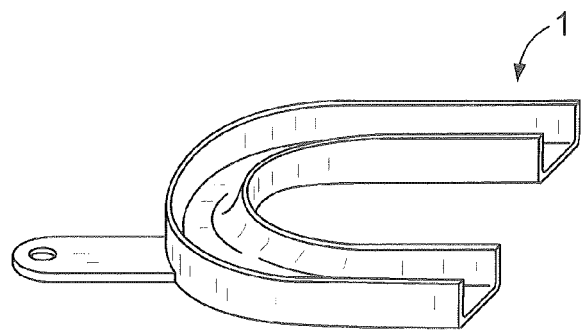
FIG. 1 shows a perspective view of an unfilled impression tray.
Figure 2:
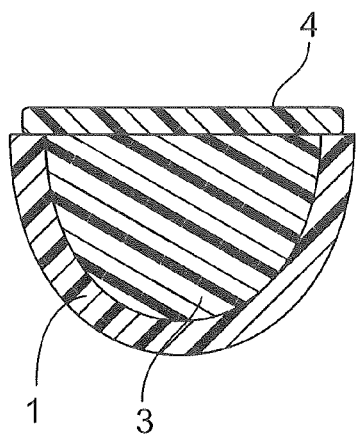
FIG. 2 shows a cross-section of a filled impression tray in accordance with a first form of embodiment of the invention.
Figure 3:
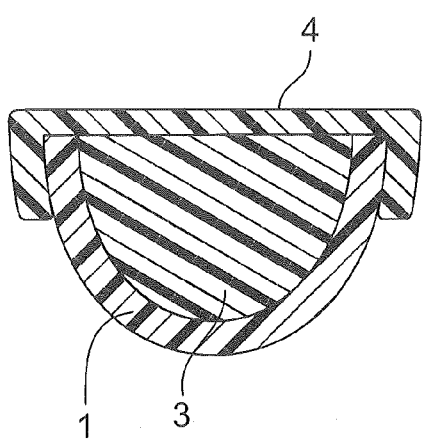
FIG. 3 shows a cross-section of a filled impression tray in accordance with a second form of embodiment of the invention.
Figure 4:
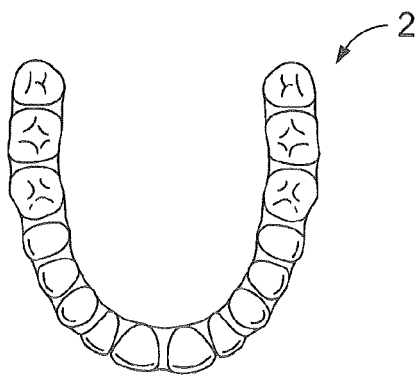
FIG. 4 shows a view of a dental splint from above.

In order to produce a dental splint 2 as shown in FIG. 4 or another dental product, the impression tray 1 can be, as shown in FIGS. 2 and 3, filled with a kneadable, plastically deformable material as the impression material 3, which has an initial viscosity at 23° C. and/or a viscosity during the procedure of more than 1000 Pa·s, preferably 1000 to 150,000 Pa·s, in particular between 1000 and 100,000 Pa·s, particularly preferably 1000 to 80,000 Pa·s. A thermoplastic film (foil) 4 is also applied onto or into impression material 3. The thermoplastic film 4 has a layer thickness of between 0.1 mm and approximately 4 mm, for example around 0.5 mm to around 2 mm. At body temperature and at room temperature the thermoplastic film 4 is solid. Only at temperatures that lie above body temperature, e.g., between 40° C. and 80° C. or up to approximately 120° C. does the thermoplastic film 4 become plastically deformable. At these temperatures the kneadable impression material 3 experiences no or only slight minor changes in viscosity, or, in the initial state it can have a tougher consistency at room temperature and only acquire a kneadable consistency at the processing temperatures that lie above it.

Impression tray 1 can be designed as a perforated tray having holes or apertures at least in its base. Said apertures can be designed such that they allow the impression material 3 to escape such that excess material can discharge from impression tray 1 and that a mechanical joint is formed between impression tray 1 and impression material 3.

Figure 5:
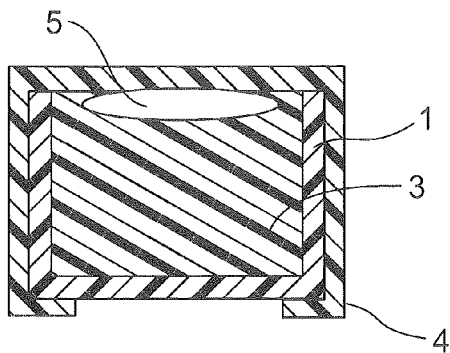
FIG. 5 shows a cross-section of a filled impression tray in accordance with a third form of embodiment of the invention and FIG. 6 shows a cross-section of a filled impression tray in accordance with a further form of embodiment of the invention.
Figure 6:
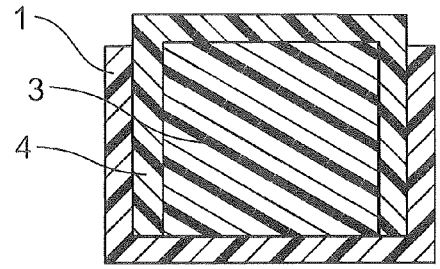
Figure 7:
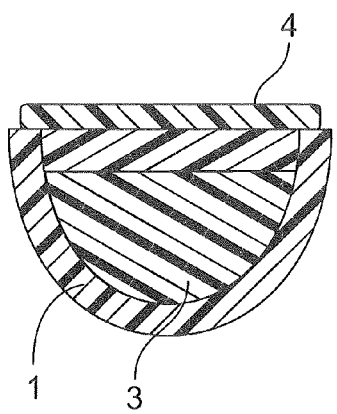
FIG. 7 shows a cross-section of a filled impression tray in accordance with a further form of embodiment of the invention.
Figure 8:
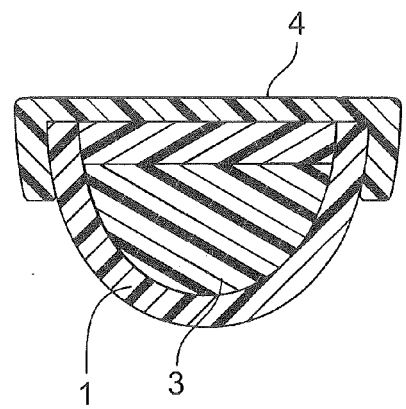
FIG. 8 shows a cross-section of a filled impression tray in accordance with a further form of embodiment of the invention.

In accordance with the embodiment shown in FIG. 2, the thermoplastic film 4 is approximately designed as a flat plate that can stand above the impression tray 1 or be cut into a horseshoe shape, essentially matching the contours of the impression tray 1. Alternatively to this, it is also possible for the thermoplastic film 4 to be placed on the impression material 3 and the impression tray 1 in such a way that, as shown in FIG. 3, it is approximately U-shaped in cross-section. For this, the thermoplastic film 4 is provided with a section approximately matched to the shape of a jaw which is arranged on the side of the impression material 3 facing away from the base. In FIGS. 3, 5 and 6 edge sections project downwards from the first section, which at least in sections are in contact with the impression tray 1, overlapping the side walls of the impression tray 1 on the inside (FIG. 6) or on the outside (FIGS. 3 and 5). As shown in FIG. 5 the edge sections of the film 4 can also overlap the impression tray 1 to such an extent that both side walls and at least part of the base of the impression tray 1 are covered. This form and arrangement of the film protects the impression material and (in the case of film applied to the outside in accordance with FIGS. 3 and 5) the impression tray. On supplying targeted heat energy to the film for a not too long period of time, the impression material and the impression tray can thereby at least be protected against heating up too strongly. Therefore essentially only the film is heated.

In order to produce a dental splint 2, the thermoplastic film 4 is heated to a processing temperature which can lie, for example, between 40° C. and 80° C. To achieve a defined degree of heating of the thermoplastic film 4 without heating the impression material 3 and/or the impression tray 1 too strongly, in one example of embodiment there is an air cushion arranged, at least in parts, between the film 4 and the impression material 3, through which the heat input into the impression material 3 is reduced. In addition to this the film 4 is specifically heated in that, more particularly, (targeted) heat energy is only supplied to the film 4.

As soon as the film 4 has reached its processing temperature and has become plastically deformable the film can be applied directly into the mouth of a patient. For this the thermoplastic film 4, together with the impression tray 1 and the impression material 3 is applied to a row of teeth or to individual teeth. When the rigid impression tray 1 filled with kneadable material is pressed against the row of teeth, the thermoplastic film 4 is deformed to match the contours of the teeth, whereby the impression material 3 exerts an even pressure on the thermoplastic film 4 on all sides.

The impression tray 1 can be removed from the mouth together with the impression material 3 and the dental splint 2. The materials of the impression material 3 and the splint 2 are selected in such a way that they do not bond with each other at the processing temperature and can be easily separated from one another. More particularly, an insulating layer (not shown in the figures) can be provided between these materials which allows the impression material 3 to be easily separated from the dental splint 2 without causing damage to the latter. It has proven to be particularly advantageous if the insulating layer is in the form of a film (not shown in the figures) that is thin compared with the thermoplastic film 4, for example in the form of a cling film, which may possibly be provided with a coating, for example a fluid coating, that reduces adhesion. The insulating layer can also reduce the heat input from the film 4 into the impression material 3 and/or the impression tray 1. Furthermore, in all forms of embodiment an air cushion 5, only indicated in FIG. 5, can be provided, at least in parts, between the first section of the thermoplastic film 4 and the impression material 3. The air cushion 5 can also be in the form of a continuous air cushion which extends at least approximately over the entire horseshoe shape, or it can consist of several smaller air cushions.

Figure 9:
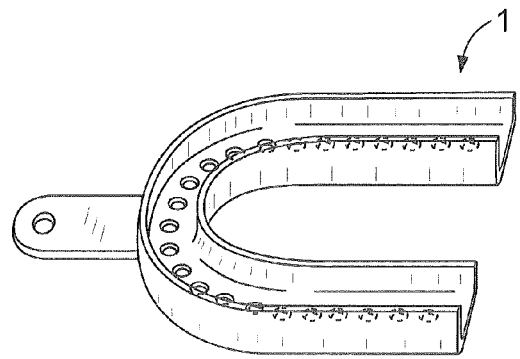
FIG. 9 shows a perspective view of an unfilled impression tray comprising a mechanical retention device.

Alternatively to this, the impression tray 1 can be initially removed from the mouth along with the impression material 3, while the dental splint 2 remains in the mouth and is removed separately. For this, the impression tray 1 can be provided with adhesives and/or mechanical retention means so that the impression material 3 can be removed from the mouth more easily together with the impression tray 1. For example, FIG. 9 illustrates a perspective view of an unfilled impression tray comprising a mechanical retention feature.

After any necessary cutting or other subsequent working, the dental splint 2 produced directly in the patient's mouth can be used as an orthodontic aligner, a bite plate, a miniature plastic splint, an occlusal splint, a healing cap, a fluidisation tray, a whitening tray, a transfer tray, a mouth protector, a positioner or a medication carrier or similar device.

Due to the stronger heating of the thermoplastic film 4 compared with the impression tray 1 and/or the impression material 3, the heat input into the mouth of the patient is overall less than in the case of uniform heating of the film, the impression material and the impression tray, even if the thermoplastic film were to be heated to high temperatures with the method according to the invention. The production of a dental splint is not therefore associated with exposure to too high temperatures in the mouth, which are experienced as unpleasant by the patients.

The invention will be described in more detail below with the aid of examples:
1. Impression Material

EXAMPLE 1

In a kneader, 43% by weight of a trimethylsilyl capped polydimethylsiloxane with a viscosity at 20° C. of 2,000,000 mPa·s, 49% by weight of a polyethylene powder (LDPE) with a mean particle size of 17 μm and 8% by weight of a white mineral oil with a viscosity of 200 mPa·s are homogeneously mixed.

A white, kneadable paste is produced which has a consistency of 24 mm (measured in accordance with ISO 4823). This impression material forms a plastically deformable agent for adapting a film, and due to its tough consistency is can be used as a functional system component in a kit in accordance with the invention for producing a dental product. The impression material is also suitable for the method in accordance with the invention for producing a dental product.

EXAMPLE 2

In a kneader, 43% by weight of a trimethylsilyl capped polydimethylsiloxane with a viscosity at 20° C. of 1,000,000 mPa·s, 52.5% by weight of a polytetrafluoroethylene powder (PTFE) with a mean particle size of 12 μm and 4.5% by weight of a white mineral oil with a viscosity of 200 mPa·s are homogeneously mixed.

A white, kneadable paste is produced which has a consistency of 24 mm (measured in accordance with ISO 4823). This impression material forms a plastically deformable agent for adapting a film, and due to its tough consistency and its high separating effect with regard to the thermoplastic splint plastic (EVA) is can be used as a functional system component in a kit and/or the method in accordance with the invention for producing a dental product.

EXAMPLE 3

In a kneader, 60% by weight of a trimethylsilyl capped polydimethylsiloxane with a viscosity at 20° C. of 1,000,000 mPa·s and 40% by weight of a polypropylene powder (PP) with a mean particle size of 38 μm are homogeneously mixed.

A white, kneadable paste is produced which has a consistency of 22 mm (measured in accordance with ISO 4823). This impression material forms a plastically deformable agent for adapting a film, and due to its tough consistency and its high degree of dimensional stability as well as its low tendency to oil separation while being stored, it can be used as a functional system component in a kit in accordance with the invention for producing a dental product and/or for the method in accordance with the invention.

2. Thermoplastic Material (Blank Mold as a Preliminary Step of an Individual Thermoplastic Dental Product)

A blank mold (pre-form), as will be described in the following examples, can, for example, be a film-like element made of thermoplastic material. This element can exhibit a geometry that is suitable for the subsequent production of a dental product, more particularly an essentially horseshoe-shaped form that is approximately U-shaped in cross-section.

EXAMPLE 4

95% by weight of a granulated ethylene-vinyl acetate copolymers with a vinyl acetate proportion of 32% and a melting point of 63° C. are homogenously premixed by hand with 5% by weight of a polycaprolactone present in granulate form with an average molecular weight of 80,000 g/Mol and a melting point of 59° C. and introduced into an injection molding system via an extruder. The injection mold parts obtained via an aluminium tool to produce a thermoplastic blank mold for the subsequent dental splint have a Shore A hardness of 62, and an optical transparency of 86% for visible light at a layer thickness of 1.7 mm.

This thermoplastic blank mold can be heated to approximately 70° C. through being exposed to a source of heat and is then thermoplastically deformable, and on cooling to approximately 37° C. it hardens to form a solid flexible molded element. A thermoplastic synthetic material produced in this way is suitable for the method in accordance with the invention of producing a dental product, more particularly for direct splint production in the mouth. The thermoplastic material can, for example, be used in a kit for producing a dental product in accordance with the invention. On the basis of its optical transparency, its mechanical properties and its plastic behaviour after heating, the material described here can, for example be used to produce a whitening splint.

EXAMPLE 5

90% by weight of a granulated low-molecular polyvinylchloride and 10% by weight of a polycaprolactone with an average molecular weight of 80,000 g/Mol and a melting point of 59° C. that is present in granulate form, are homogeneously premixed by hand and introduced via an extruder into an injection molding system. The injection mold parts obtained via an aluminium tool to produce a thermoplastic blank mold for the subsequent dental splint have a high rigidity and Shore A hardness as well as almost complete optical transparency for visible light at a layer thickness of 1.7 mm.

This thermoplastic blank mold can be heated to approximately 65° C. through being exposed to a source of heat and is then thermoplastically deformable, and on cooling to approximately 37° C. it hardens to form a solid flexible molded element. A thermoplastic synthetic material produced in this way is suitable for the method of producing a dental product in accordance with the invention and for a kit in accordance with the invention. On the basis of its optical transparency, its mechanical properties and its plastic behaviour after heating, the material described here can, for example, be used to produce a dental splint of high mechanical strength.

3. Insulating Layer (Separating Agent)

When constructing a kit for producing a dental product consisting of a rigid base tray, an impression material filled into this and a thermoplastic splint material (blank mold) arranged above these, an insulating layer (separating agent) can be incorporated between the impression material and the thermoplastic splint material which is shown in examples 6 and 7.

EXAMPLE 6

A polyethylene film (for example, household cling film Melitta Toppits 2 in 1) is used, the underside of which lies directly on the impression material and which is coated on the top side with a thin film of a trimethylsilyl capped polydimethylsiloxane with a viscosity at 20° C. of 10,000 mPa·s, whereby this coated side is partially in contact with the underside of the thermoplastic splint material.

With this arrangement, after using the thermoplastic splint set in the mouth of a patient, the molded dental splint can be very easily removed from the impression material without deformation and without leaving residues.

EXAMPLE 7

An irreversibly plastically deformable film, Hytrel 5556 by Dupont, is used with a layer thickness of 50 μm, which is applied on the underside directly on the impression material and which on its upper side is coated with a thin film of a trimethylsilyl capped polydimethylsiloxane with a viscosity at 20° C. of 10,000 mPa·s and is in partial contact with the underside of the thermoplastic splint material.

With this arrangement, after using the thermoplastic splint set in the mouth of a patient, the molded dental splint can be very easily removed from the impression material without deformation and without leaving residues, whereby the used film has the advantage that together with the thermoplastic splint synthetic material it is deformed during molding in the mouth and does not therefore exert any elastic resorting forces which could result in a poorly contoured, and therefore poorly fitting dental splint.

4. Complete System (Kit for Producing a Dental Product)

EXAMPLE 8

A thermoplastic splint set, that is to say a kit for producing a dental product, is put together consisting of a rigid injection-molded basic tray made of polypropylene, an impression material filling it in accordance with example 3, a separating layer arranged above the impression material in accordance with example 6 and a thermoplastic blank mold arranged above it in accordance with example 4.

The blank mold (pre-form) and the tray are designed in such a way that, particularly in the area of the front teeth, the film of the blank mold is not in contact with the edge, i.e. the circumferential edge facing away from the base of the tray, of the external (vestibular) tray wall. This could make adaptation of the film during molding more difficult or even prevent it, thereby impairing the quality of the molding.

This arrangement, which has been tempered to 23° C., is exposed for 90 seconds to a fan with hot air at a temperature of 130° C. During this period the thermoplastic film selectively heats up to a temperature of 65° C. and thereby becomes plastically deformable. After exposure to the hot air the temperature of the other system components is considerably lower. The impression tray is at 37° C. and the impression material at 40° C.

This selectively heated kit is applied to the lower jaw of a test subject by pressing onto the row of teeth. After a short cooling phase of approximately one minute, the splint set is removed from the mouth. As a result of the even pressing pressure of the impression material the contours of the teeth are clearly molded in the thermoplastic splint. The thermoplastic split is pulled off the basic tray and the impression material, whereby the separating agent previously incorporated in accordance with example 6 ensures that pulling off can take place without warping and leaving residues. The pulled-off thermoplastically molded film is cut off with scissors along the molded margin of the gum and is adapted to a finished splint. On repositioning on the row of teeth the produced splint fits firmly on the teeth.

Due to the high degree of optical transparency the aesthetics of the patient's teeth are only slightly impaired. A splint produced in accordance with the invention using this example can be used as a matrix for producing temporary crowns and bridges, and due to the low Shore A hardness and flexibility preferably also as whitening splints for brightening teeth.

5. Producing Dental Impressions

EXAMPLE 9

Sticky Impression Material

In a kneader 50% by weight of a trimethylsilyl capped polydimethylsiloxane with a viscosity at 20° C. of 1,000,000 mPa·s, 40% by weight of a polyethylene powder (LDPE) with a mean particle size of 17 μm, and 10% by weight of a highly dispersed silica that has been intensively dried before use and has a BET surface of 170 m²/g are homogeneously mixed.

This produces a white kneadable paste that has a consistency of 24 mm (measured in accordance with ISO 4823). Through the use of the highly dispersed silica the impression material acquires a high degree of stickiness compared with polypropylene and ethylene vinyl acetate copolymer. The high level of stickiness is also shown by the fact that the impression mass can only be removed from the contact surface with tools or with solvents.

EXAMPLE 10

Thermoplastic Blank Mold as a Preliminary Step of Molding

95% by weight of a granulated ethylene vinyl acetate copolymer with a vinyl acetate proportion of 32% and a melting point of 63° C. are homogeneously premixed by hand with 5% by weight of a polycaprolactone with an average molecular weight of 80,000 g/Mol and a melting point of 59° C. that is present in granulate form, and introduced via an extruder into an injection molding system. The injection mold parts obtained via an aluminium tool to produce a thermoplastic blank mold for the subsequent dental splint have a Shore A hardness of 62, an optical transparency for visible light of 86% with a layer thickness of 1.7 mm.

On being exposed to infrared light, this thermoplastic blank mold (pre-form) heats up to approximately 130° C., is then thermoplastically deformable, and on cooling to approximately 37° C. hardens to form a solid flexible molding element.

A thermoplastic synthetic material produced in this way is suitable for the method in accordance with the invention of selective heating through targeted energy and, independently thereof, for taking impressions in the mouth.

EXAMPLE 11

Complete Thermoplastic Impression Material System

A kit is put together consisting of an injection-molded rigid basic tray made of polypropylene, an impression material filling it in accordance with example 9 and a thermoplastic blank mold in accordance with example 10 applied above it. This arrangement, which has been tempered to 23° C., is brought to a temperature of 130° C. by means of targeted thermal energy. During this period the thermoplastic film selectively heats up to a temperature of 65° C. and thereby becomes plastically deformable. After exposure to the hot air the temperature of the other system components is considerably lower. The impression tray is at 37° C. and the impression material at 40° C. This selectively heated kit is applied to the lower jaw of a test subject by pressing it onto the row of teeth. After a short cooling period of approximately one minute the kit is removed from the mouth.

Through the even pressing pressure of the impression material the contours of the teeth are precisely molded in the thermoplastic film. In accordance with conventional dental techniques the kit is then filled with plaster. A plaster model providing an identical copy of the molded dental situation of the lower jaw is obtained with which the replacement teeth can then be produced.

6. Device for Heating Thermoplastic Material

A device in accordance with the invention for the selective heating of a thermoplastic material has an energy source, more particularly in the form of a stainless steel heater with, for example, laser-cut heat conductors with macanite insulation. Alternatively a heat radiator, a lamp (for example an infrared lamp, halogen lamp with/without reflectors), a PTC heating element, an open wire heating system on macanite carriers, ceramic field heating and/or a source of hot air can be used as a source of energy.

In addition a holder device for the kit comprising an impression tray, an impression material and the thermoplastic material to be heated is envisaged. The holder device is arranged with regard to the energy source so that essentially only the thermoplastic material is exposed to the direct heat radiation of the energy source. The kit and the energy source are arranged in such a way that the thermoplastic material faces the source of energy. This can take place, for example, in that the shape of the energy source is matched to that of the material to be heated. Thus, the energy source for heating the kit can be matched in an approximately horseshoe-like shape to the shape of the kit or the thermoplastic material which corresponds to the form of the jaw. If a suitable area of thermoplastic material is provided for molding the upper plate, a semicircular area of the energy source can also be added if necessary.

In the device in accordance with the invention one or more of the following units can also be provided:
  Heating unit for waxes (this can be implemented with a self-regulating PTC heating element),
  Electrical connection unit for machining tools, such as grinding, cutting etc.
  Unit for thermal separation, i.e. a heated blade or heated scissors to cut the thermoplastic material (including a connection and holder for the separating device).
  Holder device for fixing the kit so that it can, for example, be cut with the thermal separating device.
  Heating unit for thermoplastically deformable impression trays
  Heating chamber for agar-agar injections and/or hydrocolloid molding material
  Read unit for reading-in product and/or processing parameters, more particularly a barcode reader, which, possibly in conjunction with a control unit can carry out confirmation of originality, identification of the material group or material type, the material thickness, the processing temperature for the energy source, the heating time (possibly for different heating phases), the maximum heat retention time and/or the maximum cycle time (such a barcode can be applied to the packaging in combination with the article code, or as a single code just for setting the heating processes, e.g. applied to the film for packaging the thermoplastic splint).

Preferably a control unit is assigned to the energy source in order to allow temperature-controlled heating of the thermoplastic material. The control device can be set up in such a way that the energy source heats up the thermoplastic material in a first step at a predetermined temperature (heating phase 1 at a defined minimum temperature) and in a subsequent second step (heating phase 2: clock cycle follow-up heating) heats through the thermoplastic material with reduced energy source output. This second heating phase is for the deep heating of the thermoplastic material and takes place, for example, with the output of the energy source reduced to 20% compared with the first phase. The device can also be set up to that a drawer into which the kit is placed can only be opened on reaching the minimum temperature for heating phase 1. After the second heating phase a heat retention phase can take place for a predetermined time if the kit is not immediately removed. In order to avoid damage to the kit and/or the device, the latter can stop the heating process after a preset time and/or on exceeding a critical temperature and/or eject the kit.

The invention claimed is:
1. A method of producing a dental product, the method comprising:
  a) providing an impression tray, an impression material- and a thermoplastic material for producing a dental product, wherein the impression tray is filled with the impression material and the thermoplastic material is provided on or in the impression tray and/or the impression material;
  b) heating the thermoplastic material provided on or in the impression tray and/or the impression material to a temperature lying below 200° C. and above the softening temperature of the thermoplastic material;
  c) applying the thermoplastic material with the impression tray filled with the impression material into the mouth of a patient;
  d) applying the thermoplastic material to at least one tooth and/or the gums, for a period of time until the thermoplastic material has cooled to a temperature below its softening temperature, thereby molding a dental product; and
  e) removing of the impression tray, the impression material and the dental product formed by the thermoplastic material from the mouth of the patient,
  wherein in step b) the thermoplastic material is selectively heated through the supply of targeted energy more strongly than the impression tray and/or the impression material.

2. The method in accordance with claim 1, wherein in step b) the thermoplastic material is selectively heated by a heat radiator.

3. The method in accordance with claim 1, wherein before step b) the thermoplastic material is provided with at least one substance that improves thermal input into the thermoplastic material.

4. The method in accordance with claim 1, wherein before step b) the impression tray and/or the impression material is/are provided with a substance and/or consist(s) of a material that reduced the thermal input into the impression tray and/or the impression material.

5. The method in accordance with claim 1, wherein at least one insulating layer and/or insulating solution is provided between the thermoplastic material and the impression material.

6. The method in accordance with claim 1, wherein in step b), the heating only takes place up to a defined temperature that is indicated by a temperature indicator in and/or on the impression tray, the impression material, the thermoplastic material and/or an insulating layer.

7. The method in accordance with claim 1, wherein the thermoplastic material is provided in a form of a tube in which the impression material is contained, whereby the dental product is cut out of this after cooling of the thermoplastic 8. The method in accordance with claim 1, wherein in step e) the impression tray, the impression material and the thermoplastic material are jointly removed as one unit from the mouth of the patient.

9. A kit for producing a dental product, the kit comprising an impression tray, which is made of a material that is solid at temperatures below around 110° C., and which has a base adapted to the shape of a jaw with side walls projecting away from this base;

an impression material provided in or on the impression tray, that is plastically deformable at least at temperatures between around 10° C. and around 90° C.; and a thermoplastic film for producing a dental product which is solid at body temperature and plastically deformable by hand at a temperature between body temperature and around 150° C.;

wherein the thermoplastic film has a first section matched to the shape of a jaw that is arranged on the side of the impression material facing away from the base, and edge sections projecting away from this first section which are in contact with the impression tray at least partially overlapping the side walls of the impression tray on the inside or outside wherein the impression tray and the impression material are connected to each other mechanically and/or through an adhesive bond wherein between the first section of the thermoplastic film and the impression material an air cushion is arranged at least in parts.

10. A kit for producing a dental product, the kit comprising an impression tray, which is made of a material that is solid at temperatures below around 110° C., and which has a base adapted to the shape of a jaw with side walls projecting away from this base;

an impression material provided in or on the impression tray, that is plastically deformable at least at temperatures between around 10° C. and around 90° C.; and a thermoplastic film for producing a dental product which is solid at body temperature and plastically deformable by hand at a temperature between body temperature and around 150° C.;

wherein the thermoplastic film has a first section matched to the shape of a jaw that is arranged on the side of the impression material facing away from the base, and edge sections projecting away from this first section which are in contact with the impression tray at least partially overlapping the side walls of the impression tray on the inside or outside wherein the impression tray and the impression material are connected to each other mechanically and/or through an adhesive bond, wherein between the thermoplastic film and the impression material at least one insulating layer is provided in the form of an insulating film, insulating foil and/or insulating solution.

11. A kit for producing a dental product, the kit comprising an impression tray, which is made of a material that is solid at temperatures below around 110° C., and which has a base adapted to the shape of a jaw with side walls projecting away from this base;

an impression material provided in or on the impression tray, that is plastically deformable at least at temperatures between around 10° C. and around 90° C.; and a thermoplastic film for producing a dental product which is solid at body temperature and plastically deformable by hand at a temperature between body temperature and around 150° C.;

wherein the thermoplastic film has a first section matched to the shape of a jaw that is arranged on the side of the impression material facing away from the base, and edge sections projecting away from this first section which are in contact with the impression tray at least partially overlapping the side walls of the impression tray on the inside or outside wherein the impression tray and the impression material are connected to each other mechanically and/or through an adhesive bond, wherein the impression tray, the impression material, the thermoplastic film and/or the insulating layer has temperature indicator.

* * * * *